(12) United States Patent
Valerio et al.

(10) Patent No.: US 6,364,833 B1
(45) Date of Patent: Apr. 2, 2002

(54) IRRIGATOR FOR USE WITH SURGICAL RETRACTOR AND TISSUE STABILIZATION DEVICE AND METHODS RELATED THERETO

(75) Inventors: Michael A. Valerio, Wrentham, MA (US); Jennie H. Brown, Providence; Thomas E. Martin, Riverside, both of RI (US)

(73) Assignee: Genzyme Corpforation, Cambridge, MA (US)

( * ) Notice: Subject to any disclaimer, the term of this patent is extended or adjusted under 35 U.S.C. 154(b) by 0 days.

(21) Appl. No.: 09/481,645

(22) Filed: Jan. 12, 2000

Related U.S. Application Data

(63) Continuation-in-part of application No. 09/345,859, filed on Jul. 1, 1999.
(60) Provisional application No. 60/117,333, filed on Jan. 24, 1999.

(51) Int. Cl.$^7$ ................................................. A61B 1/32
(52) U.S. Cl. ........................ 600/232; 600/231; 600/205
(58) Field of Search ................................. 600/187, 201, 600/205, 227, 228, 231, 232, 233, 235, 37; 604/19; 606/1

(56) References Cited

U.S. PATENT DOCUMENTS

| | | | |
|---|---|---|---|
| 3,626,471 A | * 12/1971 | Florin | |
| 4,143,652 A | 3/1979 | Meier et al. | |
| 4,949,707 A | 8/1990 | Levahn et al. | |
| 5,063,908 A | * 11/1991 | Collins | |
| 5,167,223 A | 12/1992 | Koros et al. | |
| 5,242,240 A | 9/1993 | Gorham | |
| 5,513,827 A | 5/1996 | Michelson | |
| 5,514,089 A | 5/1996 | Walbrink et al. | |
| 5,624,393 A | 4/1997 | Diamond | |
| 5,727,569 A | * 3/1998 | Benetti et al. | 128/898 |
| 5,772,583 A | 6/1998 | Wright et al. | |
| 5,906,607 A | * 5/1999 | Taylor et al. | 606/1 |
| 6,015,378 A | * 1/2000 | Borst et al. | 600/37 |
| 6,033,362 A | * 3/2000 | Cohn | 600/213 |
| 6,063,021 A | * 5/2000 | Hossain et al. | 600/37 |

FOREIGN PATENT DOCUMENTS

| | | | |
|---|---|---|---|
| DE | 297 11 829 | 9/1997 | |
| DE | 197 08 587 | 11/1998 | |
| EP | 0 808 606 | 1/1997 | |
| EP | 0 791 330 | 8/1997 | |
| FR | 1019217 | 1/1953 | |
| WO | WO-97/10753 A1 | * 3/1997 | ........... A61B/17/02 |
| WO | WO 97/40738 | 11/1997 | |
| WO | WO 97/40752 | 11/1997 | |
| WO | WO 98/27869 | 7/1998 | |
| WO | WO 98/48703 | 11/1998 | |

OTHER PUBLICATIONS

Izzat, M. Bashar et al., Cardiac Stabilizer for Minimally Invasive Direct Coronary Artery Bypass, Ann. Thorac. Surg., vol. 64, pp. 570–571 (1997).

Riah Mohammad et al., A Simple Technique and Device to Provide a Bloodless Operative Field in Coronary Aratery Surgery Without Cross–Clamping the Aorta, Journal of Thoracic and Cardiovascular Surgery, vol. 66, No. 6, Dec. 1973.

\* cited by examiner

*Primary Examiner*—Jeffrey A. Smith
(74) *Attorney, Agent, or Firm*—Richard D. Allison; Thomas J. DesRosier

(57) ABSTRACT

The present invention relates to an irrigation system for use with surgical retractors and devices for stabilizing a predetermined area of the body during a surgical procedure and more particularly to an irrigation system for use with medical devices that are used in connection with minimally invasive coronary artery bypass grafting surgical procedures, and more specifically to an irrigation system for use with surgical retractors and stabilizing devices configured for use with each other for such surgical procedures wherein the irrigation system provides a controlled flow of fluid to a desired surface of the medical device to maintain a clear surgical site.

26 Claims, 5 Drawing Sheets

IRRIGATOR FOR USE WITH SURGICAL RETRACTOR AND TISSUE STABILIZATION DEVICE AND METHODS RELATED THERETO

The present application is related to U.S. Ser. No. 60/117, 33 filed on Jan. 24, 1999 and is a continuation-in-part of U.S. Ser. No. 09/345,859 filed on Jul. 1, 1999 (pending), the priority thereof is claimed hereby and the entire teachings of the above applications are incorporated herein by reference.

FIELD OF INVENTION

The present invention relates to an irrigation system for use with surgical retractors and devices for stabilizing a predetermined area of the body during a surgical procedure. The present invention is even more particularly directed to an irrigation system used in connection with cardiac procedures including coronary artery bypass grafting surgical procedures and valve replacement or repair procedures, and more specifically to an irrigation system for use with surgical retractors and stabilizing devices configured for use with each other for such surgical procedures.

BACKGROUND OF THE INVENTION

Diseases of the cardiovascular system affect millions of people each year and are a cause of death for large numbers of people in the United States and throughout the world. A particularly prevalent form of cardiovascular disease involves a reduction in the blood supply to the heart caused by atherosclerosis (coronary artery disease) or other conditions that create a restriction in blood flow at a critical point in the cardiovascular system leading to the heart.

One technique for treating such a blockage or restriction is a surgical procedure known as a coronary artery bypass graft procedure, which is more commonly known as "a heart bypass" operation. The surgical correction of occluded or stenosed coronary arteries by means of bypass grafting are probably still the most common procedures performed today, particularly when multiple grafts are needed.

In the coronary artery bypass graft procedure, the surgeon either removes a portion of a vein from another part of the body for grafting or detaches one end of an artery and connects that end past the obstruction while leaving the other end attached to the arterial supply. When using a vein from another part of the body, the surgeon installs this portion at points that bypass the obstruction. In both cases, the objective is to restore normal blood flow to the heart.

In addition, when using this conventional technique, the surgeon makes a long incision down the middle of the chest, saws through the sternum and spreads the two halves of the sternum apart. The surgeon then performs several procedures necessary to connect the surgical patient to a cardiopulmonary bypass machine to continue the circulation of oxygenated blood to the rest of the body while the heart is stopped and the graft is being sewn in place. Although such a procedure is one common technique for treatment, the procedure is lengthy, traumatic, expensive and can damage the heart, the central nervous system and the blood supply of the patient.

In an effort to reduce expense, risk and trauma to the patient, physicians have also turned to minimally invasive surgical approaches to the heart, such as intercostal and endoscopic access to the surgical site. With such procedures, the heart is beating during the surgical procedure. Thus, there is no need for any form of cardiopulmonary bypass and there is no need to perform the extensive surgical procedures necessary to connect the patient to such a bypass machine.

Many attempts at performing minimally invasive bypass grafting on a beating heart, however, have been thought of as being tedious, dangerous and difficult because of the delicate nature of the surgical procedure, the lack of adequate access and visibility through a reduced surgical field, and the lack of a convenient way to adequately stabilize and reduce tissue movement at the graft site. Because these procedures are performed while the heart muscle is continuing to beat, the blood continues to flow and the heart continues to move in three dimensional movement while the surgeon is attempting to sew the graft in place. Also, the surgical procedure to install the graft requires placing a series of sutures through an extremely small vessel and onto tissue that continues to move during the procedure. It is necessary that these sutures be fully and securely placed so the graft is firmly in position and does not leak.

There is disclosed in U.S. Pat. No. 5,730,757, an access platform for the dissection of an internal mammary artery. The described access platform has first and second blades interconnected to a spreader member that laterally drives the blades apart together and support pads interconnected to the first blade. A torsional member is operably interconnected to the first blade and the spreader member and is used to vertically displace the first blade in either direction. Thus, increasing the surgeon's working space and visual access for the dissection of the internal mammary artery. A tissue retractor interconnected to the blades is used to draw the soft tissue around the incision away from the surgeon's work area. It is further provided that the access platform can include a port that can be used to mount a heart stabilizer instrument.

There also is described in U.S. Pat. No. 5,875,782 granted to Ferrari et al. and U.S. Pat. No. 5,894,843 granted to Benetti et al. an apparatus for stabilizing the predetermined area on a heart or other organ of a patient to enable a surgical procedure on a beating heart. The apparatus includes a bifurcated member having two elongated prongs and an elongated handle. The handle segment can be movably attached to a rib retractor so that a person is not required to hold the handle segment. In one disclosed embodiment, the apparatus further includes a device to hold the bifurcated member in a desired position against the surface of the heart so that contraction of the heart does not cause either vertical or horizontal motion at the target site during the surgical procedure.

There also is described in U.S. Pat. No. 5,836,311 granted to Borst et al. an apparatus for stabilizing the predetermined area on a heart or other organ of a patient to enable a surgical procedure on a beating heart. The apparatus includes a single legged or bifurcated member having a plurality of suction members thereon which are attached to the surface of the heart using suction pressure. The arm portion of this device can be movably attached to a rib retractor or other surgical device so a person is not required to hold the handle segment and the suction device may be locked into position against the surface of the heart With any of these mechanical stabilization approaches, it is important to maintain a clear field of view for the surgeon to assist in the precise dissection of the surrounding tissue and placement of the sutures for the anastomosis. Additionally, if the surgical field is not clear, it is possible that the surgeon will not be able to adequately assess the viability of the blood vessel for the subsequent procedure. In the past, this has been accomplished by having the nurse squirt fluid onto the surgical field using a syringe containing normal saline. This practice requires the nurse to continually stop whatever else she is doing to locate and pick up the syringe and then squirt a small amount of fluid onto the surgical site as requested by the surgeon. Alternately, a separate device known as a blower/mister may be used to clear the surgical site. This device is a hand held device that is connected to a source of carbon dioxide or saline. Use of this device allows the nurse to direct the tip of the device to the desired area, but it is yet another instrument that is positioned in the surgical field and it requires the nurse to discontinue doing whatever else they may be doing to turn the device on, adjust the flow and move it to the desired location.

There is a continuing need however for improved devices and methods for providing the surgeon with an easier way to perform a very complicated surgical procedure while providing devices and methods that are inexpensive, safe and reliable.

SUMMARY OF THE INVENTION

The present invention features a system for aspirating a surgical field while retracting, stabilizing or manipulating a predetermined area of a body. The overall system includes a surgical retractor, a stabilization arm or apparatus and a tissue support or stabilization device with an irrigator thereon, and methods of use related thereto. Also featured is a system that supports any of a number of surgical implements, for example a diaphragm retractor, a valve retractor, a light or a suction device for use with an irrigator during a surgical procedure. The stabilization system and related devices that are featured herein are particularly advantageous for use in performing off-pump coronary artery bypass grafting procedures wherein the heart remains beating during the surgical procedure and/or valve repair or replacement procedures. One advantage of the present invention relates to the ability to maintain a clear surgical field during the surgical procedure.

The present invention further relates to an irrigation system for use with a surgical retractor system having a stabilization arm and a stabilization device. The present invention further includes a system for immobilizing tissue and providing a clear surgical field at the surgical site as well as a method of using the irrigation system with the stabilization arm and stabilization device during a surgical procedure. A preferred embodiment of the irrigation system and retractor system of the present invention includes a stabilization device having an aperture therein and that extends from the stabilization arm to a location that is adjacent to or surrounds the surgical site. Furthermore, a holder is used to position the nozzle of the irrigator adjacent to the desired location along the surgical site. A separate handle may be attached to or fabricated for use with the irrigator and/or the retractor system so that the user can manipulate the position and volume of fluid received from the irrigator as needed.

In a general aspect, the stabilization system of the present invention is preferably used for stabilizing a predetermined area of a patient. This preferred system includes a retractor for opening and spreading the chest of the patient, a stabilization device for locally stabilizing the predetermined area of tissue and a stabilization arm that functionally secures the stabilization device to the retractor. The retractor preferably includes a rail system having two arms and a rack segment. The rack segment interconnects the two arms, for selectively spacing the two arms from each other and for maintaining the two arms in a desired fixed relationship. In a preferred form of the present invention, the two arms and rack segment are configured to receive the connector of the stabilization arm at nearly any desired location thereon.

The stabilization device preferably includes a device of the type commonly known as the Cohn Cardiac Stabilizer marketed by the Genzyme Corporation of Cambridge Mass., although various horseshoe or suction type devices may also be used. The preferred form of the stabilization device is a generally square or rectangularly shaped member having a planar surface with centrally located opening therein. This opening is the area through which the surgeon performs the anastomosis or other procedure on the tissue of the beating heart. The stabilization device is preferably a two piece member so that once the anastomosis is completed, the pieces may be separated to remove the device from around the anastomosis. As described more fully below, flexible tapes are sutured through the tissue and then threaded through the stabilizing device. Once the stabilization device is positioned in the desired orientation and location in contact with the tissue, the flexible tapes are then pulled snug through the opening of the stabilization device to provide a system which minimizes the overall movement of the predetermined area of the tissue.

The stabilization arm of the present invention preferably includes an elongated handle having a first end and a connector thereon for releasably connecting the stabilization device to the distal end of the elongated handle. This connection allows the stabilization device to be pivotally and slidably moved to a desired position into contact with the predetermined area of the tissue of the patient while minimizing the interference of the stabilization device and stabilization arm with the field of view at the surgical site. The stabilization arm also includes a mounting mechanism or sled member which is preferably slidable along the retractor for removably securing the stabilization arm to at least one of the rails on the retractor arms and/or the rack segment of the retractor.

According to a preferred form of the present invention, the arms of the retractor are configured with a front edge and a step in the top surface thereof to form an elongated rail surface along substantially the entire length thereof. The step is preferably spaced apart a predetermined and consistent distance from the front edge and is also located on the interconnecting or rack segment of the retractor. Also, the stabilization arm preferably includes a mounting mechanism or sled member which is configured to removably engage the front edge and the step at any desired location on one or more of the arms or the rack segment of the retractor. The mounting mechanism includes a lever for selectively engaging the step and front edge on the arm or rack segment of the retractor so the mounting mechanism is removably and slidably secured to the arms or the rack segment.

In another aspect of the present invention, there is featured a surgical retractor including two arms, a rack segment and a plurality of sternal blades with at least one blade extending downwardly from each arm. Each blade includes an upper section adjacent to the bottom surface of the arm and a lower section extending distally of the arm. A slot on the bottom surface of the arms includes a tapered surface adjacent to the front edge thereof to facilitate the placement of the blades on the arms. A lip surface is also located adjacent to the slots on the bottom surface of the arms to securely retain the blades on the bottom surface of the arms during the procedure while still allowing the blades to be easily removable for initial positioning and subsequent sterilization following the procedure.

Each of these features enables the user to determine the optimum position for the stabilization arm and stabilization device while ensuring that the surgeon's view of the operative area is not unnecessarily obstructed. Additionally, these features allow the present invention to be used in many different medical procedures because of the versatility of system set up and orientation of the components of this invention.

In another preferred aspect of the present invention, the irrigation system includes a source of sterile fluid such as an IV bag of normal saline that is hung remotely from the surgical site. A flexible fluid delivery line extends from the bag, along the preferably rigid stabilization arm to a nozzle which is preferably removably attached to the handle portion of the stabilization arm on the retractor system. The fluid delivery line is preferably releasably and adjustably attached to the stabilization arm by a plurality of adjustable clamps to ensure that the delivery line is maintained away from the surgical field. Additionally, the nozzle is preferably adjustable to nearly any orientation with respect to the stabilization arm and stabilization device such that as the stabilization device is oriented to provide the optimum contact with the tissue of the patient, the nozzle may also be adjusted to provide the optimum orientation with respect to the surgical site to provide the desired flow of fluid to the surgical site without unnecessarily obstructing the surgical site or interfering with the surgical procedure.

The coronary arteries of the typical patient are about 1–2 mm in diameter, and the pumping heart can move these arteries over distances of several millimeters during each heartbeat. Therefore, movement of even 1 or 2 millimeters can result in a displacement of the grafting site that can substantially interfere with effective anastomosis, it is therefore desirable to restrain movement of the artery at the surgical site. Additionally, it is very important to keep the surgical site as clear as possible so that the surgeon may perform the anastomosis or other delicate procedure without interference from blood or other debris. Therefore, the irrigator provides an easily positionable nozzle and a flow control member to allow the location and flow of fluid to be adjusted depending on the needs and/or desires of the surgeon during the particular surgery. Additionally, the connection of the nozzle to the stabilization arm is preferably through a frictional member such that when the nozzle is aimed at the desired location, it will stay in that orientation until it is readjusted.

In another form of the present invention, the irrigation system may be connected to a regulated source of carbon dioxide to allow the user to direct a stream of carbon dioxide to the surgical site. As with the irrigation system described above, the flexible delivery line is connected to the stabilization arm by at least one and preferably two clamp members to ensure that the delivery line is maintained adjacent to the stabilization arm and does not interfere with the surgical site.

Other aspects and embodiments of the invention are more fully discussed below.

BRIEF DESCRIPTION OF THE DRAWINGS

For a fuller understanding of the nature and desired objects of the present invention, reference is made to the following detailed description taken in conjunction with the accompanying drawing figures wherein like reference numbers denote corresponding parts throughout the several views and wherein.

DESCRIPTION OF THE PREFERRED EMBODIMENT

Figure 1:
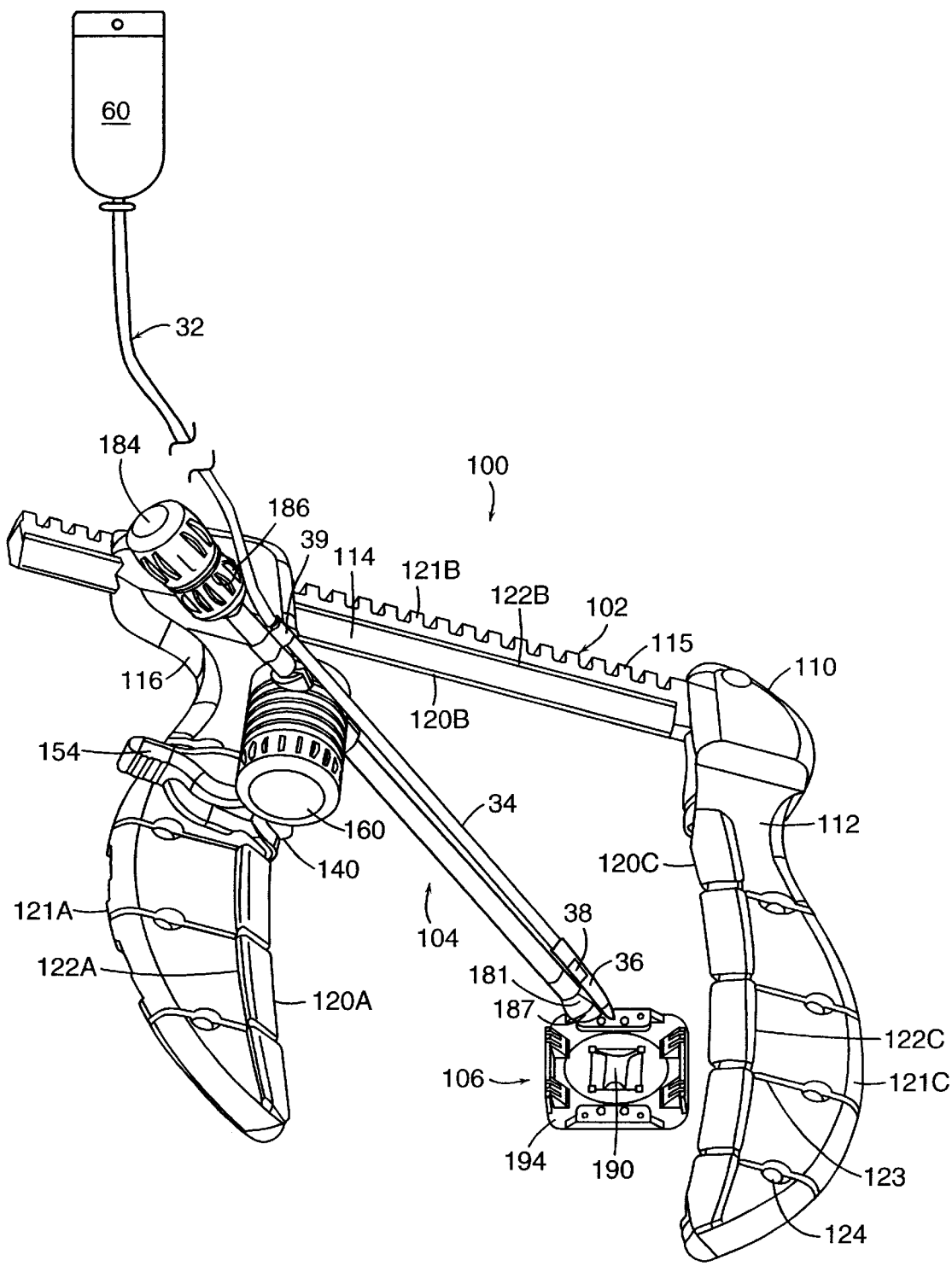
FIG. 1 is a perspective view of an irrigation and stabilization system that assists in the stabilization of a predetermined area of a body and irrigation of the surgical site according to a first aspect of the present invention.
Figure 2:
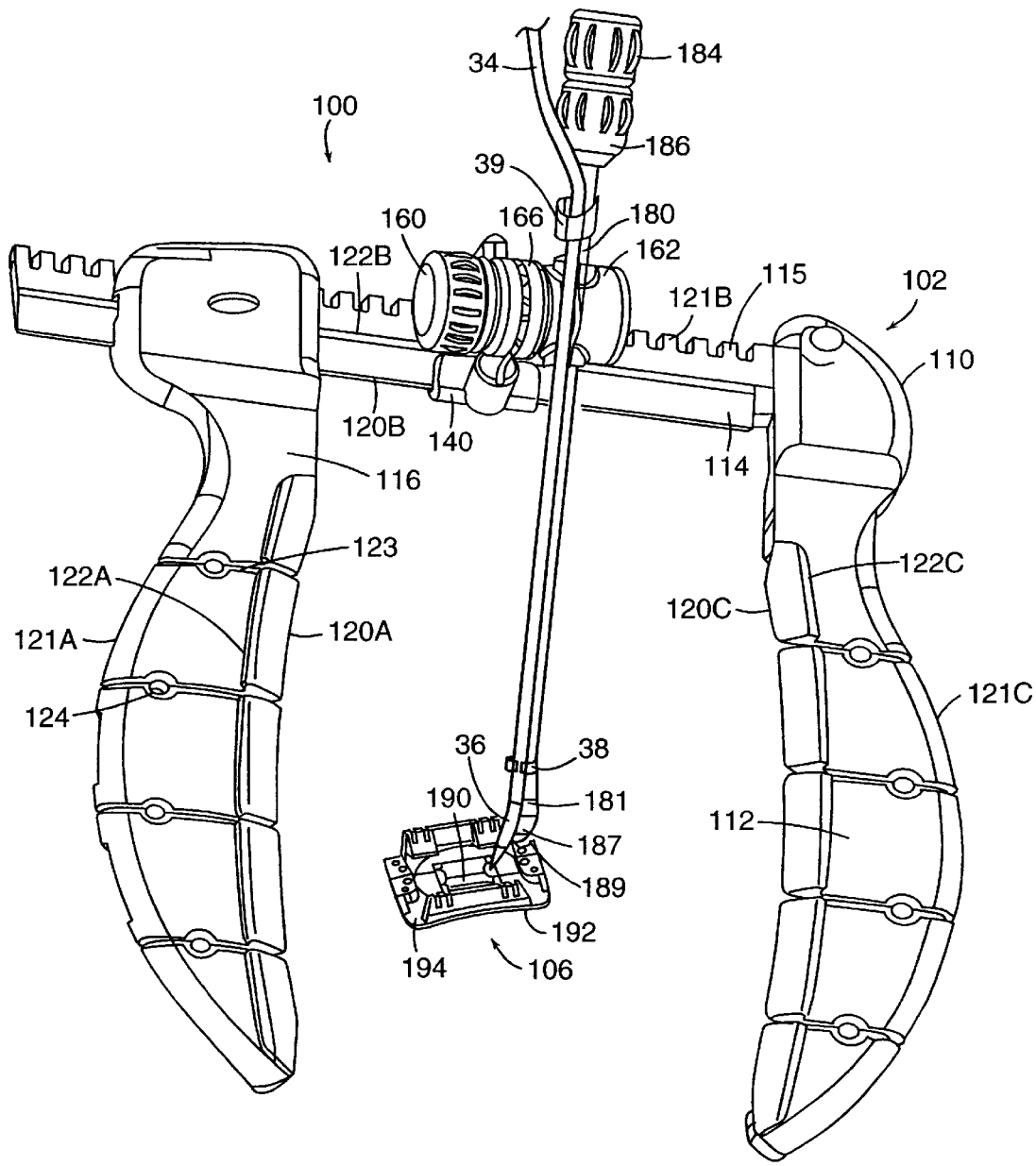
FIG. 2 is a perspective view of the irrigation and stabilization system of the present invention wherein the sled member is positioned on a rack segment of the retractor.

Referring now to the various figures of the drawings wherein like reference characters refer to like elements, there are shown various views of a preferred and alternate form of a stabilization system 100 according to the present invention. As described more fully below, the preferred embodiments of the present invention include an irrigation system for use with a stabilization system used in the stabilization of a predetermined area of a body such as the predetermined area of a heart or other organ of a patient to assist the surgeon in performing a surgical operation or procedure on a patient. The stabilization system 100 is particularly useful in connection with single or multiple vessel off-pump coronary artery bypass procedure on a beating heart through a sternotomy or mini-sternotomy incision although various other uses may be envisioned by a person skilled in this art. The irrigation system 32 is used to assist in maintaining a clear surgical field or site during the procedure.

A surgeon may use the stabilization system 100 to apply a slight contacting or compressive force on the tissue of the heart in the area where the surgical procedure will occur so the heart's movement at that specific area is diminished. In a preferred form of this invention, the stabilization system 100 is used in combination with flexible tapes, sutures or other mechanical means so that the surface of the heart is stabilized using a combination of restraining and stabilizing forces. In certain procedures, it may also be advantageous to place a traction suture around an artery using a needle and suture thread to occlude the blood vessel. These sutures may then be attached to the stabilizing device so that the flow of blood through the blood vessel is selectively restricted.

Systems for stabilizing the heart of a patient are particularly useful for various suturing techniques or procedures. One example of this type of procedure is the performance of an anastomosis for a bypass graft. In this type of procedure, the physician is attempting to suture the circumference of a blood vessel that may be about 1 mm to a moving blood vessel on the surface of the heart. Another area of use of the present invention may be in brain surgery, heart valve surgery, tissue dissection or other types of blood vessel surgery where stability is critically important to avoid disastrous consequences or where it is desirable to have a precisely defined and clear surgical field. One skilled in the art will appreciate that the present invention, although advantageously suited for heart surgery, can be used at any location on or within the body where tissue stabilization, retraction or isolation of a predetermined area is desired. This includes, but is not limited to, the liver, kidneys, bladder, stomach, intestines, brain and vascular and other soft tissue surgery. Furthermore, the irrigation system is easily attachable to various retractors or similar devices that extend into an area adjacent to the surgical field.

Referring specifically to the drawings, the stabilization system 100 according to the present invention includes a retractor 102, a stabilization sub-system or stabilization arm 104 and a stabilization device 106. The retractor 102 is specifically configured so the stabilization arm 104 can be secured thereto. The retractor 102 preferably includes a rigid L-shaped member 110 having an arm segment 112 and a rack segment 114. The retractor 102 also includes a movable second arm segment 116 having a handle 118 thereon which is movably associated with the L-shaped member 110.

The stabilization arm or sub-system 104 preferably includes an elongate handle segment 180 that may be either curved or straight and preferably interconnects the retractor 102 and the stabilization device 106. The handle segment 180 preferably includes a first end having a distal connector 181 thereon to pivotally and removably retain the stabilization device 106 thereon. The handle segment 180 is attachable to the retractor 102 by a connector such as a mounting mechanism or sled member 140. The proximal or second end of the handle segment 180 preferably includes a knob 184 thereon that is rotatable with respect to the handle segment 180. This allows the movement of the stabilization device 106 to be fixed and/or pivotal with respect to the handle segment 180 by manipulating the knob 184 on the proximal end of the handle segment 180. This arrangement also allows the stabilization device 106 to be mountable on and preferably removable from the distal connector 181.

An irrigation system 32 can be attached to the stabilization arm 104 or integrated therein and is used to remove material such as blood from the surgical site. In this particular embodiment, the irrigation system 32 is connected at one end to a fluid containing IV bag 60 and connected at a second end to a nozzle 36 that extends along the stabilization arm 104 to a location adjacent to and spaced apart from the stabilization device 106. The flexible tube 34 extends between the IV bag and the nozzle and preferably has a plurality of retaining members such as clips 38 and 39 positioned thereon to enable the flexible tube 34 and nozzle 36 of the irrigation system 32 to be positioned along the stabilization arm 104. As shown, clip 38 preferably includes a ball and socket arrangement to allow the flexible tube 34 to be clipped to the stabilization arm 104 and frictionally retained in nearly any desired position along the stabilization arm. The ball and socket arrangement is preferably designed to be a frictional fit so that as the nozzle is moved or oriented to the desired position, the nozzle will remain in the desired position without requiring the nurse or physician to hold the nozzle in the desired position. The distal end of the nozzle is preferably oriented adjacent to the stabilization device 106 to allow fluid to be directed onto the surgical site and stabilization device to remove blood or other debris from the surgical site to maintain a clear surgical field during the surgical procedure.

As shown in the drawings, clip 38 attaches the nozzle 36 to the stabilization arm 104. This clip 38 may be integral with the socket portion of the ball and socket connector or may be a separate component. The clip 38 includes a top socket section 40 that substantially surrounds and frictionally engages a ball member 42. This arrangement allows the nozzle 36 to be oriented and retained in any desired direction to provide the fluid to the desired location in the surgical site. For example, the nozzle 36 may be oriented to point upwardly or downwardly and along either side of the stabilization arm. The ball member 42 is connected to a U-shaped connector 44 that is sized to engage the stabilization arm 104. This arrangement preferably allows the clip 38 to be connected to the stabilization arm 104 and movable longitudinally along the stabilization arm. The distal end of the nozzle 36 preferably extends adjacent to or over a portion of the stabilization device 106 and more preferably drips or squirts fluid into the desired portion of the window area 190 of the stabilization device 106. It is important that the position of the nozzle 36 be versatile to match the orientation of the stabilization device 106 because the surgical site may be located on nearly any surface of the heart. Therefore, the orientation of the stabilization device may be vertical, horizontal, upside down or any combination thereof and the nozzle must be able to assume a similar orientation while allowing the fluid to flow from the nozzle onto the surgical site in order to maintain a clear surgical site. Therefore, with the preferred form of the clip 38, the nozzle may be positioned above or below or along the sides of the stabilization arm and the nozzle may be pointed at nearly any angle with respect to the stabilization arm to direct fluid to the desired location.

The other style of clip 39 is shown without the ball and socket arrangement. This clip 39 includes a U-shaped upper member 46 that receives the flexible tube 34 therein and a lower U-shaped member 48 that engages the stabilization arm 104. One or more of these clips may be used to ensure that the flexible tube 34 is retained out of the operating area of the surgeon and adjacent to the handle segment of the stabilization arm 104.

Figure 3A:
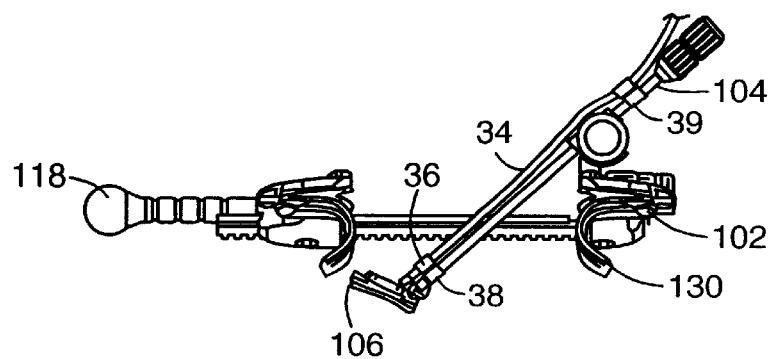
FIGS. 3A, 3B and 3C are perspective views of the various forms of the irrigation and stabilization system the present invention.
Figure 3B:
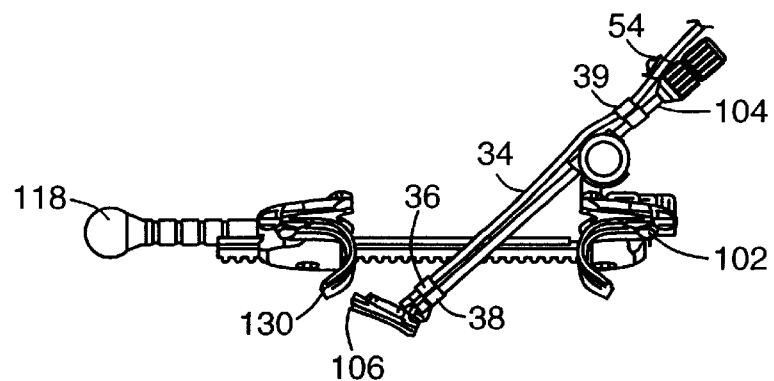
Figure 3C:
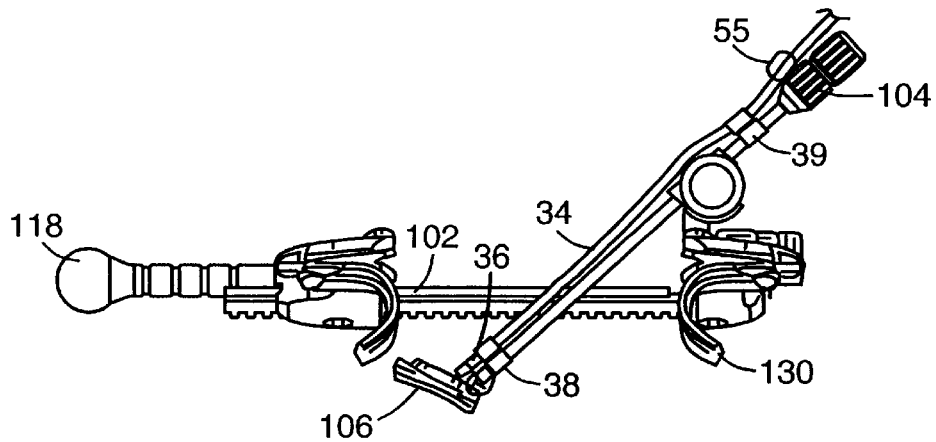
Figure 4C:
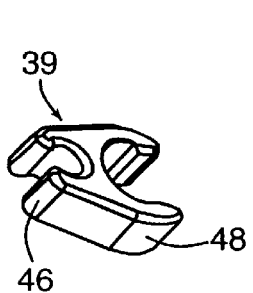
FIGS. 4A and 4B are an end view and a cross sectional view of the nozzle and distal clip of the present invention and FIG. 4C is a perspective view of the proximal clip of the preferred form of the irrigation system shown in FIG. 1.
Figure 4B:
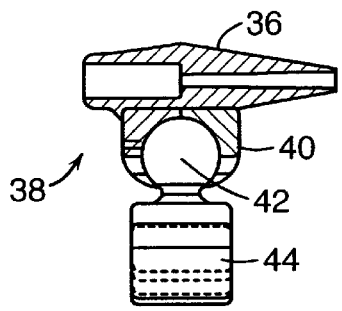
Figure 4A:
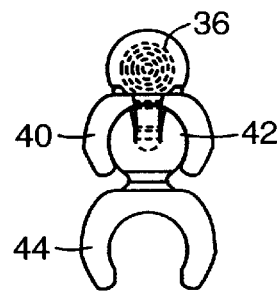
Figure 5:
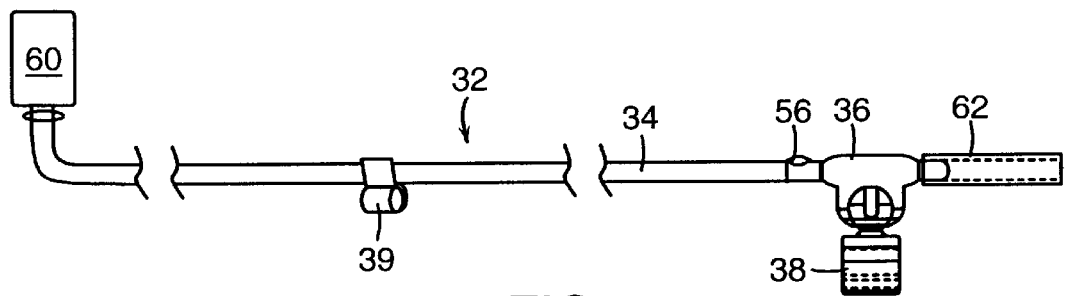
FIG. 5 is a side view of an alternate embodiment of the irrigation system of the present invention.
Figure 6:
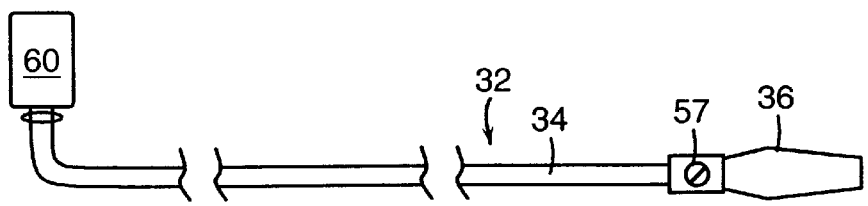
FIG. 6 is a side view of an alternate embodiment of the irrigation system of the present invention.

The flow of fluid through the irrigation system 32 may be in a free flow manner as shown in FIG. 3A or may be controlled by a standard roller valve or pinch valve located adjacent to the IV bag. Alternately and as shown in FIG. 3B, a roller type of valve 54 may be located along the length of the flexible tube 34 and proximally of the nozzle 36 to allow the nurse or surgeon to provide a controlled continuous flow of fluid therethrough. A pinch valve 55 may also be used along the length of the flexible tube 34. One desired position may be generally adjacent to the proximal end portion of the stabilization arm as shown in FIG. 3C to allow the nurse or surgeon to provide a flow of fluid to the surgical site on an as needed basis. As shown in FIG. 5, another embodiment of the present invention may include a squeeze valve 56 located along the length of the flexible tube 34. The squeeze valve 56 of this embodiment may preferably be positioned proximally of the nozzle 36 to allow the nurse or surgeon to squeeze the squeeze valve 56 using a retractor or other surgical device as additional fluid is desired to maintain a clear surgical site to provide a bolus of fluid to the surgical site individually or in addition to a steady flow of fluid. In this embodiment, the squeeze valve 56 is preferably positioned adjacent to the distal end portion of the handle segment of the stabilization arm 104. As shown in FIG. 6, an on/off valve 57 may also be used in the present invention to allow the nurse or surgeon to control the flow of fluid by adjusting the valve adjacent to the stabilization device 106 along the distal end portion of the stabilization arm 104.

Figure 7:
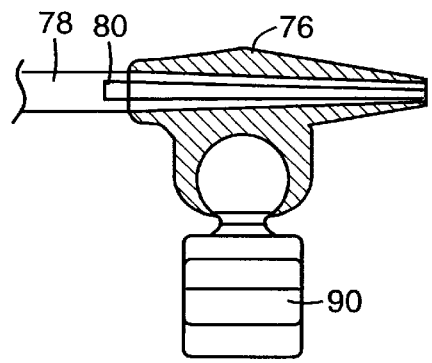
FIG. 7 is a side view, partially in cross section, of the nozzle portion of an alternate embodiment of the irrigation system of the present invention.
Figure 8:
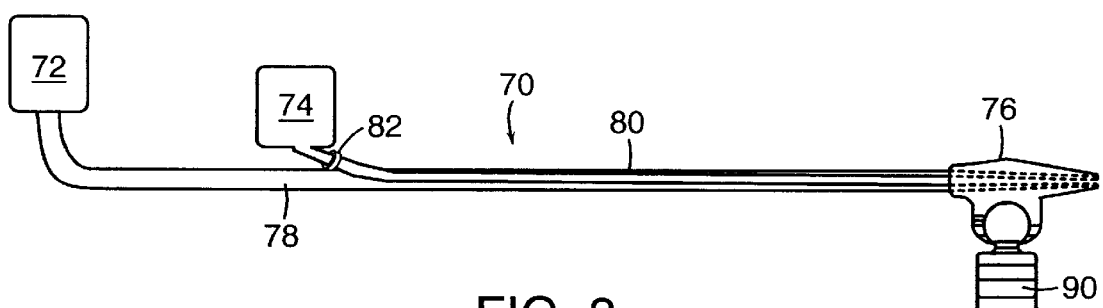
FIG. 8 is a side view of the alternate embodiment of the irrigation system of FIG. 7.
Figure 9:
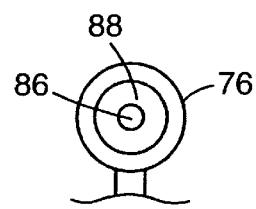
FIG. 9 is an end view of the nozzle of the alternate embodiment of the irrigation system of FIG. 7.

FIGS. 7, 8 and 9 are illustrative of another irrigation system 70 that may be attached to the stabilization arm 104 or integrated therein. In this particular embodiment, the irrigation system 70 is connected at one end to a source of carbon dioxide 72 and a source of fluid such as a fluid containing IV bag 74. The second end of the irrigation system is connected to a nozzle 76 that is positioned along the stabilization arm 104 to a location adjacent to and spaced apart from the stabilization device 106. The flexible tube 78 of this embodiment preferably includes a tubing of the type used in the prior embodiment and also includes a smaller diameter tube 80 that extends therethrough from the IV connector 82 adjacent to the IV bag 74. The smaller diameter tube 80 extends through the distal portion of the flexible tube 78 to the nozzle 76. Alternately the portion of the flexible tube extending between the IV connector 82 and the nozzle 76 may be a dual lumen tube (not shown), that preferably includes one lumen with a diameter less than the diameter of the other lumen. Therefore, in the preferred form of this embodiment, the fluid will flow through the smaller diameter tube 78 while the carbon dioxide flows through the remainder of the flexible tube 78.

As shown in FIGS. 7 and 9, the distal end of the nozzle 76 includes a smaller diameter opening 86 that is surrounded by a larger diameter opening 88. In this embodiment, the carbon dioxide preferably flows through the larger diameter opening 88 and fluid passes through the smaller diameter opening 86. As a result of this arrangement, the flow of carbon dioxide causes a venturi-type effect so the fluid is drawn from the smaller diameter opening 86. Additionally, as the fluid passes from the smaller diameter opening, it is dispersed into droplets so that a mist is applied to the desired surface of the tissue when both the carbon dioxide and fluid are used. Therefore, in this embodiment, control of the flow of the carbon dioxide will similarly control the flow of fluid to the desired tissue location. Alternately, if the flow of fluid is controlled, the amount of mist applied to the desired tissue location may be more finely controlled than with the controlled gas flow alone. Therefore, the present embodiment may be used to apply a mist of fluid; a stream of fluid; or, less desirably, a stream of gas to the desired tissue.

As with the prior embodiment, the irrigation system 72 shown in FIGS. 7–9, preferably includes a plurality of retaining members such as clips positioned therealong to enable the flexible tube 78 and nozzle 76 to be positioned along the stabilization arm 104. In this embodiment, clip 90 preferably includes a ball and socket arrangement to allow the flexible tube 78 and the nozzle 76 to be clipped to the stabilization arm 104 and frictionally retained in nearly any desired position along the stabilization arm. The ball and socket arrangement is preferably designed to be a frictional fit so that as the nozzle is moved or oriented to the desired position, the nozzle 76 will remain in the desired position without requiring the nurse or physician to hold the nozzle in the desired position.

As with the prior embodiments, the distal end of the nozzle is preferably oriented adjacent to the stabilization device 106 to allow fluid to be directed onto the surgical site and stabilization device to remove blood or other debris from the surgical site to maintain a clear surgical field during the surgical procedure.

The flow of fluid through the irrigation system 72 of this embodiment may be in a free flow manner or may be controlled by a standard roller valve or pinch valve located adjacent to the IV bag and source of carbon dioxide as discussed above. These embodiments allow the nurse or surgeon to select and adjust the desired amount of fluid flow without entering the surgical site adjacent to the stabilization device 106. The use of these valves allow the flow of fluid to be adjusted between a controlled drip and a forceful flow of fluid such that the nozzle may be positioned over the desired target area or may even be positioned beneath the desired target area and the fluid may be squirted or applied as a mist onto the surgical site as desired by the surgeon.

The preferred form of the stabilization device 106 is generally a rectangular shape having an opening or window area 190 therein. The stabilization device 106 preferably includes a bottom surface 192 that is generally planar and may include a textured surface thereon to facilitate the engagement between the stabilization device and the tissue of the predetermined area or the heart of the patient. The second surface 194 of the stabilization device 106 preferably includes a post member 196 extending therefrom. The post member 196 is preferably releasably and rotatably engaged by the distal connector 181 on the first or distal end of the handle segment 180 as described more fully below.

As described briefly above, the retractor 102 preferably includes a handle 118 located on the second arm segment 116 and the handle 118 is rotatable for displacing the two arm segments 112,116 with respect to each other. In the preferred form of this invention, rotation of the handle 118 causes a pair of posts or pinions to sequentially engage the teeth located on the outer edge 121b of the rack segment 114 to increase or decrease the distance between the first and second arms 112 and 116. The handle preferably includes a projection on the bottom surface thereof and which fits in a slot located in the retractor adjacent to the arm and rack segment to allow the user to lock the handle into position once the arms are in the desired position. This feature is particularly useful where the retractor is reused for a relatively long period of time for multiple procedures because the pinions and teeth on the retractor will gradually wear due to the pressure from the chest of the patient. As the wear occurs, the pressure from the sternum may cause the arms to move towards each other unless the arms or handle are retained in a locked position. In a specific illustrative embodiment, the rack segment 114 is configured with a finochetti type of rack as is known to those skilled in the art. In conjunction with the handle 118, the rack segment 114 and movable second arm 116 form a rack and pinion type of means for displacing the arm segments 112, 116 with respect to each other. As shown, this type of rack segment 114 includes a plurality of laterally extending teeth members 115 that engage the posts or similar tooth engaging members located in operative contact with the handle 118 of the second arm segment 116. It is anticipated that a variety of mechanisms may be used to move the second arm segment 116 along the rack segment 114. For example, a gear mechanism, a slide and locking mechanism or similar arrangement may be used to accomplish the separation and fixation of the second arm 116 with respect to the first arm 112. It is within the scope of the present invention, however, for the retractor 102 to be configured or designed with any of a number of means known to those skilled in the art for selectively displacing the first and second arm segments, 112 and 116 either towards or away from each other in a parallel, obtuse or acute angled manner.

At least one arm segment and preferably each arm segment, 112 and 116 respectively, and the rack segment 114 are configured so as to each have a front edge surface 120a, 120b and 120c extending along the inner surface of each element of the retractor 102 such that the front edges of each of the arms and the rack segment face each other. The retractor 102 also preferably includes an outer edge surface 121a, 121b and 121c extending along the outer surface of the first and second arms, 112 and 116 respectively, of the retractor 102. A step surface 122a, 122b and 122c extends along the top surface of the first and second arms, 112 and 116 respectively, and the rack segment 114 in a spaced apart relationship with respect to the front edges of each of the surfaces of the first and second arms and the rack segment to form an elongate lip or external rail surface on the arms and rack segment of the retractor. The step surface 122*a*–*c* is preferably located a preset distance back from the front edge and forms an acute angle facing away from the front edge thereof on each of the arms and the rack segment. As described hereinafter, the front edge surfaces 120*a*–*c* and the step surfaces 122*a*–*c* on the top surface of the arms and rack segment are particularly arranged and configured to face each other and so that the mounting mechanism or sled member 140 can be readily secured to the retractor 102 by engaging the front edge surface (120*a*, 120*b* or 120*c*) and the associated step surface (122*a*, 122*b* or 122*c*) on each of the first and second arms, 112 and 116, and the rack segment 114.

The preferred form of the present invention includes front edge surfaces 120*a* and 120*c* of the first and second arm segments that are of a preferably slightly concave orientation such that the mid point of the first and second arms are spaced apart from each other a greater distance than the distance of either or both of the inner or outer ends of the first and second arms, 112 and 116. Additionally, the outer edge surfaces 121*a* and 121*c* of each arm preferably has a greater curvature than the front edge surfaces 120*a* and 120*c* of the same arm so that as the retractor 102 spreads the chest of the patient, the motion of separating the first and second arms, 112 and 116, is emphasized to increase the amount the chest of the patient is spread. Therefore, at a given distance of separation between the first and second arms, 112 and 116, the midpoints of the outer surface of the arms will be separated a further distance than at the ends adjacent to the rack segment or at the ends furthest from the rack segment 114 due to the overall generally clam shell shaped configuration of the preferred form of the present invention. An advantage of this configuration is that the surgeon is provided with an opening in the sternum of the patient that is wider in the center than along the edges so that the most common area of work for the surgeon is larger than with a conventional retractor for the same amount of separation.

Additionally, the top surface of each of the arms, 112 and 116, preferably include a plurality of slots 123 extending generally perpendicular to the lengthwise dimension of each arm. These slots 123 extend from the front edge surfaces 120*a* and 120*c*; through the step surfaces 122*a* and 122*c*; and to the outer edge surfaces 121*a* and 121*c*, respectively on each of the first and second arms, 112 and 116. These slots 123 are configured to extend through the front edge surface 120*a* and 120*c* of each arm, 112 and 116, to allow the sled member 140 to be moved therealong while not cutting or interfering with any sutures that may be positioned in the slots. Additionally, each of the slots 123 preferably include a through hole 124 in communication with the slot and extending through the arm. In the preferred use of the present invention, the slots 123 are used to position sutures that have been threaded through the pericardium of the patient therein so that the pericardium or other tissue is retracted and held out of the line of sight of the surgeon by the sutures to better expose the heart of the patient.

With the preferred form of the present invention, the sutures and clamps are retained out of the working area of the surgeon. The portion of the through hole 124 adjacent to the top and bottom surfaces of the arm are preferably tapered so that distal end of the clamps or other instruments that are used to hold the sutures may be placed and retained therein during the procedure. By allowing the distal ends of the instruments to be placed into the through holes 124, the sutures are held in a secure position during the procedure and may be adjusted as needed at any time by lifting the instrument and then reclamping the suture or releasing the clamp and then pulling the suture through the clamp and subsequently closing the clamp while it remains in the through hold. Additionally, it is anticipated that some surgeons may use these through holes to suture the retractor to the patient to minimize possible extraneous movement of the retractor during the procedure.

In an exemplary embodiment of the present invention, the bottom surface of each of the first and second arms, 112 and 116, on the retractor 102 include removable sternal blades 130 attached thereto. Each blade 130 is removable so as to facilitate the use of the retractor in a full or mini-sternotomy procedure by allowing for the selective positioning and spacing of the blades 130 as desired for the particular procedure as well as for resterilization of the retractor 102 and blades 130. As illustrated, the blades 130 are positioned along the bottom surface of the arms 112 and 116 and are preferably pivotal in the horizontal and vertical directions with respect to the arms. The blades 130 are slidable into elongate ridged slots on the bottom surface of the first and second arms, 112 and 116. The blades 130 may swivel a limited distance and are selectively positioned in the slots so as to evenly distribute the retraction forces or pressure along the contour of the sternum of the patient. An upper section of each blade 130 is particularly configured to facilitate the insertion of the blades into the retractor. In particular, the upper section of the blade 130 is configured so that an upward extending and generally oblong shaped lip member is received in the ridged slots located on the bottom surface of the first and second arms, 112 and 116. This surface may also include a raised ball member which slides in a further slot located in the ridged slots. The ball member is preferably slightly depressible so that it may be slid beyond the further slot so that during the initial placement of the retractor, the blades may be positioned to extend nearly linearly along each arm in an insertion position. As the arms are retracted, the inner and outermost blades move to a retraction position to assume a slightly curved shape. In the preferred form of the present invention, the retraction position generally approximates the anatomy of the patient and allows the pressure of the sternum of the patient to be evenly distributed among the blades. The use of the ball member and the further slots and the ridged slots allow the blades to temporarily assume the linear configuration and also rise slightly to provide a lower profile and maintain the retraction edge. Once the blades are inserted into the sternum, the slight release of pressure during the insertion allows the ball member to return to the innermost end of the further slot and the blades may pivot slightly in the vertical and horizontal directions so that the blades follow the slightly curved shape of the retraction position and provide optimum leverage to retract the sternum of the patient. The upper section of the blade 130 extends generally along the bottom surface of the first and second arms, 112 and 116 and is positioned so the blade 130 extends a short distance inwardly of the front edge surfaces 120*a* and 120*c* of the arms 112 and 116. The blades 130 also include a lower section which extends downwardly from the upper section of the blade 130 in a curved manner to extend beneath the bottom surface of the retractor to readily engage the sternum of the patient. The lower section also preferably curves backward a short distance towards the outer edge surface 121 of the first and second arms, 112 and 116, to form a blade 130 having an overall C or L shape that facilitates the positioning and retention of the sternum of the patient adjacent thereto. Therefore, the blades 130, in conjunction with the displacement of the first and second arms result in the desired retraction of the tissue, bone etc. for the surgical procedure.

The stabilization sub-system or stabilization arm 104 of the present invention preferably includes an elongate handle segment 180 that interacts with the retractor 102 and the stabilization device 106. The handle segment 180 is attachable to the retractor 102 by a connector such as a mounting mechanism or sled member 140. The handle segment 180 is preferably a rigid tubular member that may be straight or curved at angle that is preferably less than about 30 degrees and more preferably about 26 degrees. The handle segment 180 includes a distal connector 181 on the distal end thereof to pivotally and removably retain the stabilization device 106 thereon and the proximal end of the handle segment 180 preferably includes a movable knob 184 and a fixed knob 186 thereon. In the preferred embodiment, the movable knob 184 is threadedly connected to the proximal end of the handle segment 180. The fixed knob 186 is fixed proximally of the movable knob 184 on the handle segment 180 to allow the user to rotate the stabilization device 106 and handle segment 180 by manipulating the fixed knob 186 when the stabilization device 106 is connected to the distal connector 181 of the handle segment 180.

The distal connector 181 consists of a generally bulbous member having an elongate slot extending through at least one side thereof. The slot is sized to allow the post member of the stabilization device 106 to pass laterally therethrough to allow the stabilization device to be easily mounted on or removed from the stabilization arm 104 through the slot while not allowing the post member of the stabilization device to pass distally from the slot. Additionally, the use of the bulbous shape on the post member and the complementary shape of the slot allow the stabilization device to be pivotal and rotatable about the handle segment. This flexibility in positioning allows the surgeon to readily position the stabilization device 106 in the desired position and against nearly any surface of the heart of the patient.

The stabilization device 106 is fixed in the desired position relative to the handle segment 180 by rotating the movable knob 184 with respect to the handle segment and/or the fixed knob. The preferred, generally pear-like, shape of the distal connector 181 and the opening in the slot optimize the connection between the distal connector 181 and the post member to enable the stabilization device 106 to be selectively retained within the distal connector 181 while allowing for the pivotal and rotational movement necessary for the use of this device in a cardiac application where space is at a premium and the device must be as versatile as possible to accommodate the surgeons needs without undue experimentation.

The stabilization arm 104 of the preferred embodiment also includes a sled member 140 operatively connected thereto. The sled member 140 is configured so the surgeon has multiple axis positioning capability for the stabilization device 106 while requiring a minimum of manipulation. In an exemplary embodiment, the bottom section of the sled member 140 includes a front edge lip, a movable second lip and an actuator lever 154. The actuator lever 154 is pivotally connected to an elongate slot in the second lip by a pin which is preferably offset with respect to the axis of rotation of the actuator lever 154 so that movement of the actuator lever 154 causes the second lip to move towards and away from the front edge lip. The front edge lip is configured so that the interior of this lip conforms generally to the shape and configuration of any of the front edge surfaces 120a–c of the retractor. The front edge lip also includes a portion that extends backwards under the front edge surfaces 120a–c of the arms and/or rack segment of the retractor so the front edge lip preferably forms an acutely angled surface that is easily secured at any location on any of the front edge surfaces 120a, 120b or 120c of the retractor 102. The actuator lever 154 is preferably positioned on the side of the sled member 140 which is adjacent to the outer edge surface 121a–c of the retractor 102 so as to not interfere with the operative field or vision of the surgeon.

In the preferred embodiment of the present invention, the sled member 140 also includes an upper section including a knob 160, a stabilization arm clamp, a sled pin clamp, and a threaded rod therein. This portion of the sled member 140 provides the surgeon with the rotational movement of the stabilization arm 104 in a combination of horizontal and vertical directions as well as allowing for the sliding and rotational movement of the handle segment 180 therethrough, all of which are advantageously controlled by the operation of the single knob 160 that is located along the periphery of the operative field.

This arrangement enables the bottom section of the sled member to be rotatable with respect to the upper section of the sled member 140 independently of whether or not the sled member is locked into position along the arms and/or rack segment of the retractor. Additionally, this orientation places the upper section of the sled member preferably directly above the front edge of the retractor as shown. This orientation significantly increases the range of motion of the sled member and therefore the range of motion of the stabilization arm and ultimately significantly increases the versatility and range of motion of the stabilization device. For example, rotation of the sled member 140 and rotation of the stabilization arm 104 will allow the user to position the stabilization device 106 beneath the arms and/or rack segment by allowing the aperture which contains the handle segment to extend inwardly of the front edge 120 of the retractor 102 and the sled pin.

The use of the stabilization system 100 according to the preferred aspect of the present invention can be best understood from the following discussion with reference to the drawings. Although the following discussion makes reference to the use of the stabilization system specifically in connection with a coronary artery bypass grafting surgical procedure, the use of the irrigation system of the present invention is not limited to such uses.

After appropriately preparing and positioning the patient for the surgical procedure and completing those actions required in advance of the use of the stabilization system, the arms 112 and 116 of the retractor 102 would be closed such that the upper portion 134 of the blades 130 are generally abutting each other. The surgeon then positions the lower sections 138 of each of the blades adjacent to the incision and pushes down on the retractor or otherwise manipulates the blades and the patient so the blades are pushed through the incision and past the sternum.

After inserting the retractor, the surgeon displaces the two retractor arm segments 112, 116 with respect to each other by rotating the handle 118 on the second arm segment 116. As the surgeon opens the sternum of the patient, they also release any underlying connective tissue and open the pericardium surrounding the heart of the patient. In order to provide for visualization of the heart, the pericardium that surrounds the heart is retracted by placing sutures (not shown) through the pericardium and then threading the sutures through the slots 123 on the retractor arms to ensure that the sutures are spaced apart from the operative field. As mentioned above, the clamps (not shown) holding the sutures may then be positioned in the slots so that the distal end of the clamping instrument is positioned in the through holes 124. This allows the sutures and clamps to be positioned out of the way of the surgeon for the subsequent procedure. After performing any subsequent actions to further open the sternum of the patient to create the desired field of view and assess the viability of the heart to perform the bypass grafting procedure on one or more vessels, the surgeon mounts the stabilization arm 104 onto one of the retractor arm segments 112,116 or the rack segment 114 in the position that they anticipate will provide the best access while minimizing the obstruction of their view for the particular procedure.

The irrigation system 32 may be attached to the stabilization arm 104 prior to this step or at this time to align the nozzle 36 to extend beyond the distal end of the stabilization arm 104 and preferably adjacent to the intended orientation of the stabilization device 106. In this particular embodiment, the flexible tube 34 of the irrigation system 32 is connected at one end to a fluid containing IV bag 60 and connected at a second end to a nozzle 36. The flexible tube 34 extends along and is connected to the stabilization arm 104. Preferably clip 38 is connected adjacent to the distal end portion of the stabilization arm 104 and one or more clips 39 are connected to the stabilization arm 104 adjacent to the proximal end thereof.

It should be recognized that the bypass grafting procedure may involve the arteries or branches thereof on nearly any surface of the heart including the posterior or backside of the heart. Therefore, having the capability to mount the combination of the stabilization arm and irrigation system to the rack segment 114 or either of the arms, 112 or 116, of the retractor can be particularly advantageous. With the preferred form of the present invention, the stabilization arm 104 and irrigation system 32 may be positioned near the top of the operative field on the rack segment 114 rather than only along the sides of the operative field. The retractor 102 is typically arranged on the body so the throat of the retractor faces the head of the patient and the surgeon is typically located on one side of the patient while a nurse is located on the other side of the patient and instruments are passed across the body of the patient throughout the procedure. Therefore, with the preferred form of the present invention, the surgeon has an additional surface to choose from when they are deciding which surface will provide the best access to the desired surface of the heart while not interfering with the procedure.

To mount the stabilization arm 104 onto the retractor 102, the surgeon rotates the sled actuator lever 154 so the second lip is oriented in a disengaged position and is spaced from the front edge lip of the sled member 140. The surgeon then positions the sled member 140 on the retractor 102 at any of a number of available positions on the arms, 112 and 116, or the rack segment 114 by positioning the front edge lip over the front edge of the selected arm or rack segment. With the preferred configuration of the sled member 140, the surgeon need not slide the sled member along the entire length of a retractor arm or be required to select from a limited number of predetermined positions, but can place the sled member 140 directly at the desired position. In this way, a surgeon can removably position the sled member 140 and irrigation system 32 anywhere on the rack segment 114 or the arms 112, 116 of the retractor 102 without having to first assemble the retractor with a sled member 140 initially positioned in any of these predefined areas. Another advantage of this configuration is that the surgeon may initially position the sled member 140 in a position that they anticipate will be close to where they will ultimately want it. If during the procedure, a different location is needed or provides better access, the surgeon may either slide the sled member 140 along the previously selected arm or rack segment to the desired location or they may remove the sled member 140 from the retractor and try various locations to see which location on the arms and rack segment provides the best access for the particular procedure. In addition, such a sled configuration also allows the surgeon to perform certain surgical procedures without having to worry about the sled member 140 cutting or interfering with any sutures that may be passing over the retractor while positioning the sled member 140. Furthermore, if multiple blood vessels are operated on or access to multiple surfaces is desired, the orientation of the sled member may be readily adjusted to accommodate the needs of the particular part of the procedure. The irrigation system 32 of the present invention allows the surgeon to disconnect the flexible tube 34 from the IV bag 60 so that as the stabilization arm 104 is moved to the different locations, the clips 38 and 39 will retain the flexible tube 34 and nozzle 36 adjacent to the handle segment and the two components may be easily repositioned without having to disconnect and subsequently reconnect the irrigation system from the stabilization arm 104 each time the stabilization device 106 is repositioned.

The surgeon may then fix the sled member in place by positioning the front edge lip of the sled member 140 over the front edge surface 120a, 120b or 120c on the desired area of the retractor 102 and then rotating the sled actuator lever 154 partially or fully, as desired, so the second lip contacts and engages the vertical extending surface of the corresponding step surface 122a–c on the retractor 102. Once the surgeon has placed the sled member on the retractor, they may then initially position the stabilization device 106 near the ultimate desired location along the surface of the heart by loosening the movable knob 184 and rotating the fixed knob 186 and also loosen the knob 160 on the sled member to orient the stabilization device 106 and stabilization arm 104 in the tentative desired position. It should be recognized that this process may be repeated as often and whenever necessary to modify the position of the stabilization device 106 at the desired location or area of the heart.

Thereafter, the surgeon may loosen knob 160 and rotate the top section of the sled member 140 about the sled pin and also move the handle segment 180 lengthwise and/or rotationally with respect to the sled member 140 to position the handle segment within the stabilization arm clamp through aperture so as to position the stabilization device 106 with respect to the predetermined area of the heart to be stabilized. Once the stabilization device 106 is in the desired contacting relationship with the predetermined area of the heart, the surgeon may tighten the knob 160 of the stabilization arm 140 so as to prevent further rotation about the threaded rod and the sled pin and also to prevent sliding of the handle segment in the sled member. The surgeon may also tighten the knob 184 of the handle segment 180 so as to tighten the connection between the distal connector 181 on the handle segment and the post member on the stabilization device 106 prevent further motion of the stabilization device 106 about the end of the stabilization arm 104. Finally, the surgeon may reconnect the flexible tube to the IV bag 60 and adjust the nozzle 36 of the irrigation system 32 to ensure that the flow of fluid is directed to the desired location in the surgical site. This location will vary depending on the target site and orientation of the stabilization device 106 and therefore, the use of a frictional contacting member such as the ball and socket arrangement in the clip 38 is important to allow the nozzle 36 to be placed in the desired orientation and to ensure that it will remain there throughout the procedure. Fine adjustment of the nozzle may also be accomplished by moving the nozzle with the end of nearly any surgical instrument so that the flow of fluid is directed to the desired surface. Additionally, as shown in FIG. 5, a nozzle extension 62 may be used to further extend the end of the nozzle to the desired location. The nozzle extension 62 is preferably a semi-rigid member that may be bent into the desired orientation and will remain there until it is removed or readjusted by the nurse or surgeon.

After completing the surgical procedure, the surgeon may remove the stabilization arm 104, irrigation system 32 and stabilization device 106 by separating the stabilization device 106 and then essentially reversing the above described steps. Alternately, the surgeon may simply release the actuator lever 154 and remove the entire stabilization arm and remaining portion of the stabilization device from the operative field. Similarly, the actuator lever may be moved to a position between the engaged and disengaged positions so that the stabilization arm may be moved out of the way while a subsequent procedure is performed or to attach a new stabilization device thereon.

In the foregoing discussion, the irrigation system of the present invention is described in terms of being used on or in combination with a stabilization device. It is within the scope of the present invention, however, for the irrigation system to be configured for use with any of a number of surgical instruments. Additionally, although one stabilization arm and irrigation system is described as being in use at a time, it is within the scope of the present invention for a multiplicity of irrigation systems and stabilization arms to be secured to the retractor or to use the irrigation system in combination with or as a blower wherein a gas such as carbon dioxide is used to blow the debris away from the surgical site.

Although a preferred embodiment of the invention has been described using specific terms, such description is for illustrative purposes only, and it is to be understood that changes and variations may be made without departing from the spirit or scope of the following claims.

What is claimed is:

1. A system for use in a surgical procedure, comprising:
   a retractor having a plurality of retractor arms thereon and a segment interconnecting said retractor arms wherein said retractor arms are movable with respect to each other;
   a stabilization arm operatively positionable with respect to said retractor and said stabilization arm being sized to hold a medical device in a desired position during a medical procedure;
   a stabilization device operatively positioned on said stabilization arm; and
   an irrigation system having a nozzle thereon and wherein said nozzle is sized to be positioned adjacent to said stabilization device and wherein said irrigation system has a retaining member thereon for removable attachment of said irrigation system to said stabilization arm.

2. The system of claim 1 wherein said retaining member includes a ball and socket member for the frictional adjustment of the orientation of said nozzle member relative to said stabilization device.

3. The system of claim 1 wherein said irrigation system includes a flexible tube sized to extend generally along the lengthwise dimension of said stabilization arm and said flexible tube is retained along said stabilization arm.

4. The system of claim 1 wherein said irrigation system includes an actuatable member therein to control the flow of a fluid through said irrigation system.

5. The system of claim 4 wherein said irrigation system includes a distal portion having said nozzle thereon and a proximal portion in flow communication with a source of fluid.

6. The system of claim 5 wherein said irrigation system further includes a flexible tube extending between said proximal and distal portions of said irrigation system and said flexible tube is engaged along at least a portion of said stabilization arm.

7. The system of claim 4 wherein said stabilization arm includes distal and proximal end portions and said nozzle of said irrigation system is sized to extend beyond said distal end portion of said stabilization arm.

8. A system for use in a surgical procedure, comprising:
   a retractor having a plurality of retractor arms thereon and a segment interconnecting said retractor arms wherein said retractor arms are movable with respect to each other;
   a stabilization arm operatively positionable with respect to said retractor and said stabilization arm being sized to hold a medical device in a desired position during a medical procedure;
   a stabilization device operatively positioned on said stabilization arm; and
   an irrigation system having a nozzle thereon and wherein said nozzle is sized to be positioned adjacent to said stabilization device and wherein said stabilization arm includes distal and proximal end portions and said irrigation system includes a plurality of retaining members thereon to removably attach said irrigation system to said stabilization arm and wherein a first retaining member is attached to said distal end portion of said stabilization arm.

9. A system for use in a surgical procedure, comprising:
   a retractor having a plurality of retractor arms thereon and a segment interconnecting said retractor arms wherein said retractor arms include a front edge surface and are movable with respect to each other;
   a stabilization arm having distal and proximal end portions and said stabilization arm is operatively positionable with respect to said retractor and sized to hold a medical device in a desired position during a medical procedure; and
   an irrigation system mountable on said stabilization arm wherein said irrigation system includes proximal and distal end portions and said distal end portion is sized to extend to a location generally adjacent to said medical device and wherein said irrigation system further has a retaining member thereon for removable attachment of said irrigation system to said stabilization arm.

10. The system of claim 9 wherein said irrigation system includes a source of fluid or gaseous material connected to said proximal end portion and a flexible tube extending between said distal and proximal end portions wherein at least a portion of said flexible tube is sized to extend along said stabilization arm.

11. The system of claim 9 wherein said irrigation system further includes an actuatable member thereon to selectively control the flow of fluid or gas from the source therethrough.

12. The system of claim 11 wherein said irrigation system includes a flexible tube and distal and proximal end portions and said proximal end portion includes a retaining member thereon to attach said irrigation system to said stabilization arm and said flexible tube includes a clamp thereon to control the flow of fluid therethrough.

13. The system of claim 12 wherein said clamp is a roller-type clamp to control the flow of fluid or gas from the source therethrough.

14. The system of claim 12 wherein said clamp is a squeeze-type clamp to control the flow of fluid or gas from the source therethrough.

15. A system for use in a surgical procedure, comprising:
a retractor having a plurality of retractor arms thereon and a segment interconnecting said retractor arms wherein said retractor arms include a front edge surface and are movable with respect to each other;
a stabilization arm having distal and proximal end portions and said stabilization arm is operatively positionable with respect to said retractor and sized to hold a medical device in a desired position during a medical procedure; and
an irrigation system mountable on said stabilization arm wherein said irrigation system includes proximal and distal end portions and said distal end portion is sized to extend to a location generally adjacent to said medical device and wherein said irrigation system includes a plurality of retaining members thereon to removably attach said irrigation system to said stabilization arm.

16. A system for use in a surgical procedure, comprising:
a retractor having a plurality of retractor arms thereon and a segment interconnecting said retractor arms wherein said retractor arms include a front edge surface and are movable with respect to each other;
a stabilization arm having distal and proximal end portions and said stabilization arm is operatively positionable with respect to said retractor and sized to hold a medical device in a desired position during a medical procedure; and
an irrigation system mountable on said stabilization arm wherein said irrigation system includes proximal and distal end portions and said distal end portion is sized to extend to a location generally adjacent to said medical device and wherein said irrigation system includes a flexible tube extending between the proximal and distal end portions thereof and a nozzle is attached to said distal end portion thereof and said proximal end portion includes a clamp thereon to control the flow of fluid therethrough and said flexible tube includes at least one retaining member thereon to releasably attach said irrigation system to said stabilization arm.

17. A system for use in a surgical procedure, comprising:
a retractor having a plurality of retractor arms thereon and a segment interconnecting said retractor arms wherein said retractor arms are movable with respect to each other;
a stabilization arm operatively positionable with respect to said retractor and said stabilization arm being sized to hold a medical device in a desired position during a medical procedure;
a stabilization device operatively positioned said stabilization arm and said stabilization device having at least one laterally extending surface sized to contact and at least partially stabilize a selected portion of the heart tissue of a patient; and
an irrigation system having a nozzle thereon and wherein said nozzle is sized to be positioned adjacent to said laterally extending surface of said stabilization device and wherein said irrigation system has a retaining member thereon for removable attachment of said irrigation system to said stabilization arm.

18. The system of claim 17 wherein said irrigation system includes a flexible tube sized to extend generally along the lengthwise dimension of said stabilization arm.

19. The system of claim 17 wherein said irrigation system includes a manually actuatable clamp member therein to control the flow of a fluid through said irrigation system.

20. The system of claim 17 wherein said irrigation system includes a distal portion having said nozzle thereon and a proximal portion in flow communication with a source of fluid.

21. The system of claim 20 wherein said irrigation system further includes a flexible tube extending between said proximal and distal portions of said irrigation system.

22. A system for use in a surgical procedure, comprising:
a retractor having a plurality of retractor arms thereon and a segment interconnecting said retractor arms wherein said retractor arms are movable with respect to each other;
a stabilization arm operatively positionable with respect to said retractor and said stabilization arm being sized to hold a medical device in a desired position during a medical procedure;
a stabilization device operatively positioned on said stabilization arm and said stabilization device having at least one laterally extending surface sized to contact and at least partially stabilize a selected portion of the heart tissue of a patient; and
an irrigation system having a nozzle thereon and wherein said nozzle is sized to be positioned adjacent to said laterally extending surface of said stabilization device and wherein said irrigation system has a retaining member thereon for removable attachment of said irrigation system to said stabilization arm.

23. The system of claim 22 wherein said clip member includes a ball and socket member for the frictional adjustment of the orientation of said nozzle member relative to said stabilization device.

24. A system for use in a surgical procedure, comprising:
a retractor having a plurality of retractor arms thereon and a segment interconnecting said retractor arms wherein said retractor arms are movable with respect to each other;
a stabilization arm operatively positionable with respect to said retractor and said stabilization arm being sized to hold a medical device in a desired position during a medical procedure;
a stabilization device operatively positioned on said stabilization arm and said stabilization device having at least one laterally extending surface sized to contact and at least partially stabilize a selected portion of the heart tissue of a patient; and
an irrigation system having a nozzle thereon and wherein said nozzle is sized to be positioned adjacent to said laterally extending surface of said stabilization device and wherein said stabilization arm includes distal and proximal end portions and said irrigation system includes a plurality of clip members thereon to removably attach said irrigation system to said stabilization arm and wherein a first clip is attached to said distal end portion and a second clip is attached to said proximal end portion of said stabilization arm.

25. A system for use in a surgical procedure, comprising:
- a retractor having a plurality of retractor arms thereon and a segment interconnecting said retractor arms wherein said retractor arms are movable with respect to each other;
- a stabilization arm operatively positionable with respect to said retractor and said stabilization arm being sized to hold a medical device in a desired position during a medical procedure;
- a stabilization device operatively positioned on said stabilization arm and said stabilization device having at least one laterally extending surface sized to contact and at least partially stabilize a selected portion of the heart tissue of a patient; and
- an irrigation system having a nozzle thereon and wherein said nozzle is sized to be positioned adjacent to said laterally extending surface of said stabilization device and wherein said irrigation system includes a flexible tube extending between the proximal and distal end portions thereof and said nozzle is attached to said distal end portion thereof and said irrigation system includes a clamp thereon to control the flow of fluid therethrough and said distal end portion and said proximal end portions include clips thereon to releasably attach said irrigation system to said stabilization arm such that said nozzle extends beyond said stabilization arm and is adjacent to said laterally extending surface of said stabilization device.

26. A system for use in a surgical procedure on a human patient, comprising:
- an elongate arm member sized to extend from a location outside of the body of a patient to a location inside the body of a patient adjacent to a surgical site;
- an irrigation system having a nozzle thereon and wherein said nozzle is sized to be positioned adjacent to the surgical site; and
- a retaining member on said irrigation system sized for the removable attachment of said irrigation system to said elongate arm member wherein said retaining member includes an adjustable member thereon for the frictional adjustment of the orientation of said nozzle member relative to said elongate arm member whereby said adjustable member enables said nozzle of said irrigation system to be movable relative to said elongate arm member when said irrigation system is attached to said elongate arm member.

* * * * *

UNITED STATES PATENT AND TRADEMARK OFFICE
CERTIFICATE OF CORRECTION

PATENT NO. : 6,364,833 B1
DATED : April 2, 2002
INVENTOR(S) : Michael A. Valerio et al.

It is certified that error appears in the above-identified patent and that said Letters Patent is hereby corrected as shown below:

Title page,
Item [56], OTHER PUBLICATIONS, "Riah Mohammad et al.", replace "Aratery" with -- Artery --;

Column 1,
Line 7, replace "60/117,33" with -- 60/117,333 --;
Line 50, replace "stemum" with -- sternum --;

Column 19,
Line 45, replace "and a nozzle" with -- and said nozzle --;

Column 20,
Line 36, replace "system has a retaining member" with -- system has a clip member --

Signed and Sealed this

Fifteenth Day of October, 2002

Attest:

Attesting Officer

JAMES E. ROGAN
Director of the United States Patent and Trademark Office